United States Patent [19]

May

[11] Patent Number: 4,791,914

[45] Date of Patent: Dec. 20, 1988

[54] ENDOTRACHEAL DEVICE

[76] Inventor: Stephen C. May, 15-A Yesteroaks Cir., Greensboro, N.C. 27408

[21] Appl. No.: 41,980

[22] Filed: Apr. 24, 1987

[51] Int. Cl.⁴ .................................................. A61B 1/26
[52] U.S. Cl. .................................... 128/10; 128/760; 604/35; 604/76
[58] Field of Search .................. 128/10, 11, 200.26, 128/760; 604/19, 35, 54, 56, 76, 93, 118–121, 319, 902

[56]  References Cited

U.S. PATENT DOCUMENTS

| 2,700,973 | 2/1955 | Ju | 604/76 |
| 3,039,463 | 6/1962 | Dickey et al. | 604/119 |
| 3,050,062 | 8/1962 | Ulmer | 604/76 |
| 3,065,749 | 11/1962 | Brass | 604/35 |
| 3,460,395 | 8/1969 | Shaw | 128/760 |
| 3,674,404 | 7/1972 | Burlis et al. | 425/326 |
| 3,855,997 | 12/1974 | Sauer | 128/760 |
| 4,321,921 | 3/1982 | Laszczower | 604/35 |
| 4,334,538 | 6/1982 | Juhn | 128/760 |
| 4,455,140 | 1/1984 | Joslin | 128/760 |
| 4,662,367 | 5/1987 | Gore | 604/319 |

OTHER PUBLICATIONS

Meconium Aspirator, Catalog No. 0101.
Pediatrics, Apr. 1987.

Primary Examiner—Max Hindenburg

[57]  ABSTRACT

The present invention comprises a disposable endotracheal device specifically for use with newborn infants. The device incorporates a conventional endotracheal tube with a fluid receptacle whereby during use, liquid withdrawn from the infant does not come in contact with the user thereby preventing exposure to a dangerous virus or the like.

3 Claims, 2 Drawing Sheets

ENDOTRACHEAL DEVICE

BACKGROUND OF THE INVENTION

1. Field Of The Invention

The present invention relates to a medical apparatus for insertion in the trachea for treatment of breathing ailments of humans and particularly for the treatment of infants.

2. Description of the Prior Art and Objectives of the Invention

Oftentimes during the treatment of human patients medical personnel come into contact with the body fluids of the patients. While sometimes this is not harmful, with the recent rise and rapid spread of the Acquired Immunodeficiency Syndrome (AIDS) virus, such contact may be fatal. Thus, many procedures which have conventionally been employed must now be changed in an effort to protect doctors, nurses and other medical professionals and technicians during patient treatment to prevent such exposure and contact.

A common procedure for newborn infants with respiratory complications includes the removal of meconium contaminated amniotic fluid from the infant's trachea by employing a endotracheal tube. A conventional procedure has been to insert the endotracheal tube through the mouth of the infant, advance the tube into the trachea and thereafter by applying mouth suction to the end of the tube meconium contaminated amniotic fluid can be removed from the trachea which prevents the infant from suffering serious damage to his lungs due to meconium contaminated fluid which is very corrosive to the lung tissue. Sometimes during this procedure the medical personnel inadvertently receives a small amount of the withdrawn liquid into his mouth. With the spread of certain virus such as hepatitis B or AIDS, such contact can prove deadly and in order to avoid this, mechanical aspirators have been attached recently to endotracheal devices which apply a mechanical suction controlled by thumb movement over a suitably positioned aperture in the suction line. However, mechanical aspirators are oftentimes not suitably controllable which can result in damage to the internal tissues or organs of the infant and it has been found that some medical personnel or operators prefer to control the suction force by using mouth suction instead of the mechanical devices. Furthermore mechanical aspirators are dependent on availability of a vaccuum suction line. Even if a suction line is available it has to be in working condition and the mechanical suction device has to be properly placed into the suction line. All this takes time and very often delivery of an infant with meconium contaminated amniotic fluid is an emergency situation without prior notice and suction of the trachea must be provided with great speed prior to an infant taking his first breath and there is not time left to prepare the mechanical suction device in working order.

In view of the danger of using conventional mouth suction devices the present invention was conceived and one of its objectives is to provide an endotracheal device which is safe for use both to the infant and to the medical operator.

It is another objective of the present invention to provide an endotracheal device which prevents withdrawn liquids from entering the mouth of the operator.

It is still another objective of the present invention to provide an endotracheal device which is available for use immediately during emergencies and does not require time consuming preparatory steps prior to its use.

It is yet another objective of the present invention to provide an endotracheal device which is relatively easy to learn to operate accurately and which is inexpensive to manufacture.

It is still yet another objective of the present invention to provide an endotracheal device in which the withdrawn liquid can be easily seen, measured and stored.

Various other objectives and advantages of the present invention will become apparent to those skilled in the art as a more detailed explanation is presented below.

SUMMARY OF THE INVENTION

The endotracheal device as presented herein is particularly useful in removing meconium contaminated fluid from the trachea of newborn infants. The invention utilizes a conventional endotracheal tube having a flange member. The flange member is received in a receptacle socket of a fluid receptacle. The fluid receptacle is formed from a clear plastic and includes a series of markings which designates cc's of fluid. A suction pipe is attached through a cap at the top of the fluid receptacle and the user places the suction pipe in his mouth and by applying suction creates negative pressure in the fluid receptacle, liquid contained within the trachea of the infant is drawn into the fluid receptacle for storage or discarding. In order to prevent the liquid from passing along the suction pipe into the mouth of the operator, the fluid receptacle has a conduit contained therein which has a bent or curved upper tip which allows the liquid to descend from the top of the receptacle and thereby separates the gas or air from the liquid to thereby prevent a virus which may be contained within the liquid from reaching the mouth of the operator. Also a fluid absorbing filter is placed in the suction pipe to insure that no liquid reaches the operator's mouth.

DESCRIPTION OF THE PREFERRED EMBODIMENT

Figure 1:
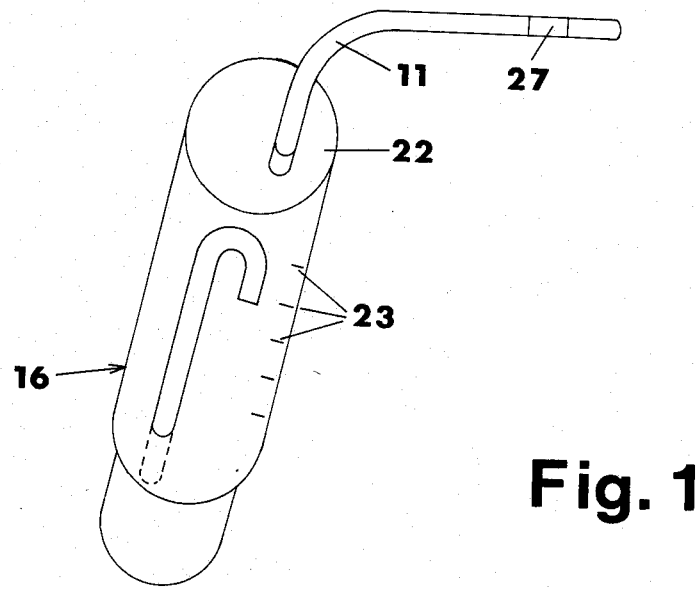
FIG. 1 demonstrates a top front perspective view of the fluid receptacle.
Figure 2:
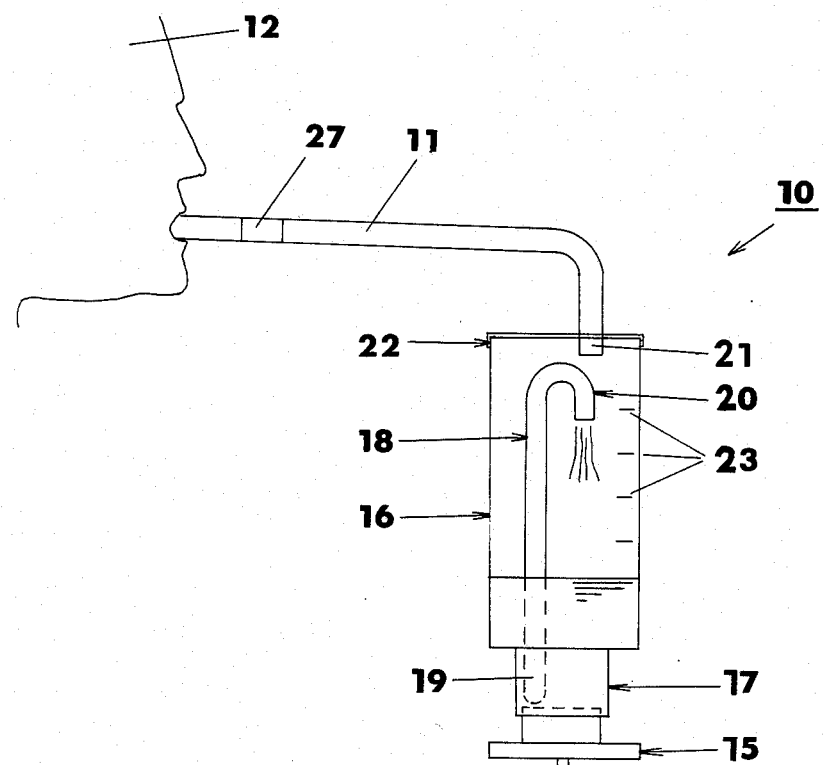
FIG. 2 shows the endotracheal device in use.
Figure 2:
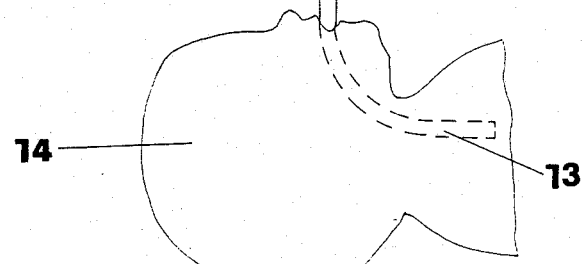
Figure 3:
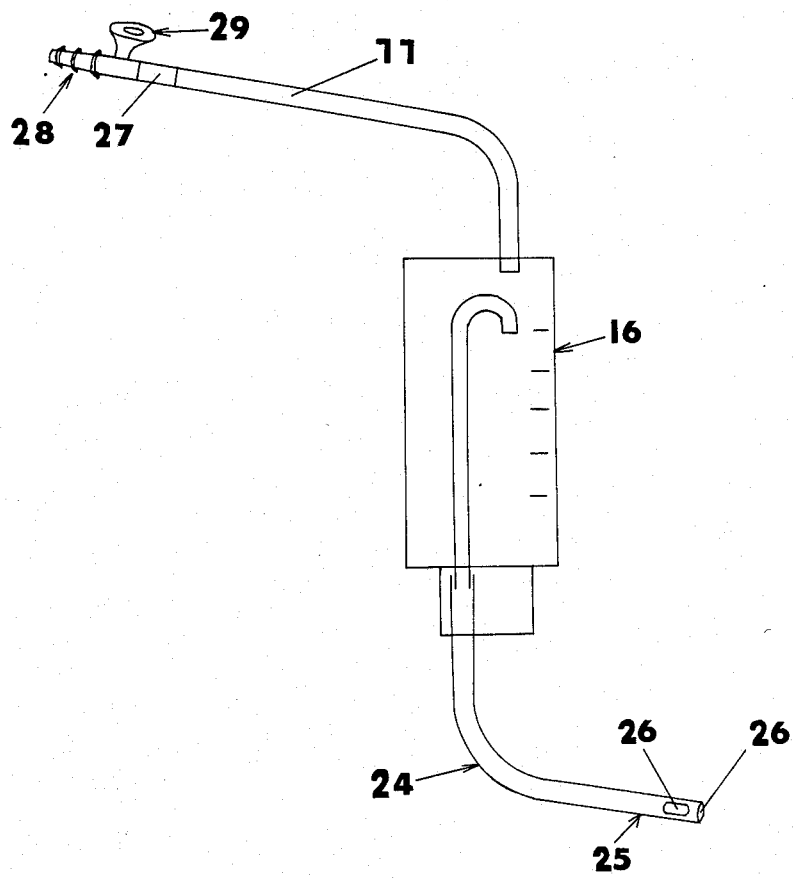
FIG. 3 demonstrates a view of the endotracheal device which may be used to remove foreign matter from the mouth to clear the view to visualize the trachea prior to insertion of the endotracheal tube into the trachea.

The preferred embodiment of the invention is shown in FIG. 2 whereby an operator such as a medical doctor applies suction to the upper most pipe of the endotracheal device whereby liquid is drawn through the trachea of the infant below and is contained within the storage receptacle. By spacing the suction pipe inside the fluid receptacle from the receptacle conduit which is shown with a inverted J-shape, all the withdrawn liquid falls to the lower portion of the fluid receptacle whereby only gases are drawn into the mouth of the operator. Any inadvertent liquids entering the suction tube are trapped by the filter on the suction pipe and are prevented from entering the operator's mouth.

DETAILED DESCRIPTION OF THE DRAWINGS AND OPERATION OF THE INVENTION

As hereinbefore mentioned, any dangerous and deadly virus such as hepatitis B or AIDS are contained within certain body fluids and may be within the body fluids of newborn infants thereby severly limiting and requiring changes in conventional medical procedures. In order to intubate infants, endotracheal tubes with flange members are conventionally used with suction applied thereto. The present invention demonstrates a new approach to limiting the spread of virus contamination whereby the liquids which contain the virus are separated and stored while gases can be drawn into the mouth of the operator without harm.

Endotracheal device 10 as shown in FIG. 2 includes suction pipe 11 which is placed within the mouth of the operator 12 which may be a medical doctor. With suction applied by operator 12 applied, tracheal fluids enter endotracheal tube 13 shown within infant 14 where they pass through flange member 15 and into fluid receptacle 16. Fluid receptacle 16 has affixed at its bottom or lower end a receptacle socket 17 which frictionally engages flange member 15. Inverted J-shaped receptacle conduit 18 is contained within fluid receptacle 16 whereby liquid passing through endotracheal tube 13 will enter lower end 19 of receptacle conduit 18 and will pass upwardly through curved free end 20 whereby the liquid falls therebelow and the gases are drawn upwardly through suction pipe 11 and pass though fluid absorbing filter 27 which can also prevent liquids from entering the mouth of the operator. Thus, liquids which carry a virus are contained within fluid receptacle 16 and are of no danger to operator 12. It has been found that terminal end 21 of suction pipe 11 is best positioned vertically above end 20 of receptacle conduit 18 in order to insure that liquid does not enter suction pipe 11. Suction pipe 11 is tightly fitted within cap 22 and fluid receptacle 16 includes a series of markings 23 thereon. Markings 23 are used to determine the amount of liquid withdrawn.

It is oftentimes necessary to remove foreign matter such as blood, mucus or other materials from the mouth of a newborn infant in order to be able to visualize his trachea prior to inserting the endotracheal tube into the trachea for removal of fluids from the trachea. In FIG. 3, the endotracheal device is shown with the endotracheal tube and flange member removed and with a flexible tube 24 attached thereto. Tube 24 includes a plurality of openings 26 at its free end 25 and can be inserted into the mouth of a newborn infant and by suction applied to suction pipe 11 blood, mucus or other materials can be withdrawn into fluid receptacle 16 without fear of such liquids passing into the mouth of the operator. As further seen in FIG. 3, suction pipe 11 includes a conventional aspirator tip 28 having thumb control opening 29. Thus if tip 28 were connected to a mechanical suction device (not shown) control of the suction pressure applied to suction pipe 11 would be carried out by partially or totally covering opening 29 with the operator's thumb.

Various other changes and modification can be made to the invention as presented herein and the descriptions are for illustrative purposes only and not intended to limit the scope of the appended claims.

I claim:

1. An endotracheal device comprising: an endotracheal tube, one end of said endotracheal tube joined to a flange member, a cylindrical fluid receptacle, said receptacle having a socket at the bottom end for receiving said flange member, a receptacle conduit, said conduit contained within said receptacle and said receptacle conduit extending from said socket terminating within said socket and spaced from said endotracheal tube, said conduit having an inverted J-shaped upper end, said receptacle having a cap at the top end opposite said socket, a suction pipe, said suction pipe passing through said cap in fluid communication with said receptacle, said suction pipe positioned vertically above and spaced from said receptacle conduit, a fluid absorbing filter, said filter attached to said suction pipe whereby applying suction to said suction pipe causes fluid to be drawn through said endotracheal tube for containment in said fluid receptacle.

2. An endotracheal device as claimed in claim 1 wherein said endotracheal device is formed from plastic.

3. An endotracheal device as claimed in claim 1 wherein said endotracheal tube comprises a flexible tube having a plurality of openings proximate its terminal.

* * * * *